United States Patent [19]

Peglion et al.

[11] Patent Number: 5,464,834
[45] Date of Patent: Nov. 7, 1995

[54] N-SUBSTITUTED N'-HETEROBICYCLIC PIPERAZINES HAVING PHARMACEUTICAL ACTIVITY

[75] Inventors: Jean-Louis Peglion, Le Vesinet; Bertrand Goument, Viroflay; Mark Millan, Paris; Jean-Michel Rivet, Nanterre, all of France

[73] Assignee: Adir et Compagnie, Courbevoie, France

[21] Appl. No.: 75,679

[22] Filed: Jun. 11, 1993

[30] Foreign Application Priority Data

Jun. 12, 1992 [FR] France .................... 92 07065

[51] Int. Cl.⁶ .................... A61K 31/495; C07D 495/04; C07D 407/14; C07D 405/10
[52] U.S. Cl. .................... 514/254; 544/376; 544/377; 549/29; 549/50; 549/51; 549/68; 549/79
[58] Field of Search .................... 514/254; 544/376, 544/377

[56] References Cited

U.S. PATENT DOCUMENTS

| | | | |
|---|---|---|---|
| 3,808,212 | 4/1974 | Renth et al. | 544/377 |
| 4,335,126 | 6/1982 | Kleeman et al. | 544/394 |
| 4,782,061 | 11/1988 | Kruse et al. | 514/254 |
| 5,242,925 | 9/1993 | Boettcher et al. | 514/254 |

OTHER PUBLICATIONS

Francis, *Cortical Pyramidal Neurone Loss May Cause Glutamatergic Hypoactivity and Cognitive Impairment in Alzeheimer's Disease: Investigative and Therapeutic Perspectives*, Journal of Neurochemistry vol. 60, No. 5, 1589–1604, 1589 (1993).
Dijk, *NMDA–Induced Glutamate Release From Rat Cortical Pyramidal Neurones is Potentiated by a 5–HT$_{1A}$ Antagonist*, Br. J. Pharmacol. 112, 10P (May 1994).
Carli, *8–Hydroxy–2–(di–n–Propylamino)Tetralin Impairs Spatial Learning in a Water Maze: Role of Postsynaptic 5–HT$_{1A}$ Receptors*, Br. J. Pharmacol. 105, 720–726 (1992).
Bowen, *Circumscribed Changes of the Cerebral Cortex in Neuropsychiatric Disorders of Later Life*, Proc. Natl. Acad. Sci. USA 86, 9504–9508 (1989).
Rodgers, *Anxiolytic–like Effect of (S)–Way 100135, a 5–HT$_{1A}$ Receptor Antagonist, in the Murine Elevated Plus–Maze Test*, European Journal of Pharmacology 261, 321–325 (1994).
Millan, *5–Hydroxytryptamine (HT)$_{1A}$ Receptors and the Tail–Flick Response. II. High Efficacy 5–HT$_{1A}$ Agonists Attenuate Morphine–Induced Antinociception in Mice in a Competitive–Like Manner*, Journal of Pharmacology and Experimental Therapeutics vol. 256, No. 3, 983–992 (1991).
Kellar, *Stimulation of Serotonin$_{1A}$ Receptors Increases Release of Prolactin in the Rat*, Neuropharmacology vol. 31, No. 7, 643–647 (1992).
Chaouloff, *5–HT$_{1A}$ and Alpha–2 Adrenergic Receptors Mediate the Hyperglycemic and Hypoinsulinemic Effects of 8–Hydroxy–2–(di–n–Propylamino)Tetralin in the Conscious Rat*, Journal of Pharmacology and Experimental Therapeutics vol. 243, No. 3, 1159–1166 (1987).
Millan, *S 14671: A Naphtylpiperazine 5–Hydroxytryptamine$_{1A}$ Agonist of Exceptional Potency and High Efficacy Possessing Antagonist Activity at 5–Hydroxytryptamine$_{1C/2}$ Receptors*, Journal of Pharmacology and Experimental Therapeutics 262 No. 2, 451–463 (1992).

Tricklebank, *The Involvement of Subtypes of the 5–HT$_1$ Receptor and of Catecholaminergic Systems in the Behavioral Response to 8–Hydroxy–2–(Di–n–Propylamino–)Tetralin in the Rat*, European Journal of Pharmacology 106, 271–282 (1984).
Aulakh, *Food Intake, Neuroendocrine and Temperature Effects of 8–OH–DPAT in the Rat*, European Journal of Primary Examiner—Emily Bernhardt
Attorney, Agent, or Firm—Gordon W. Heuschen

[57] ABSTRACT

New N-substituted N'-heterobicyclic piperazines corresponding to the general formula I:

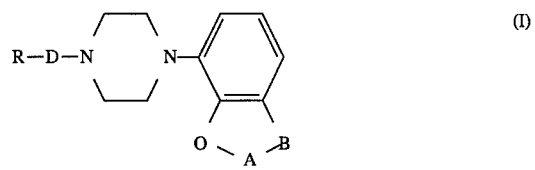

wherein:

R represents:

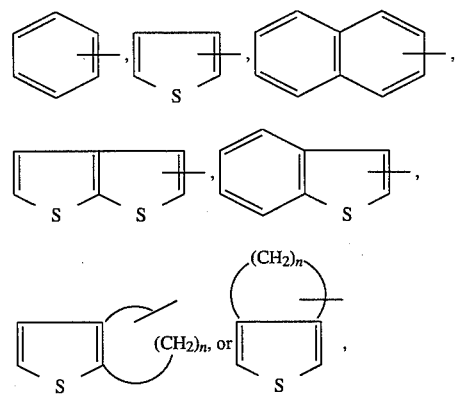

D represents a single bond, except when R represents naphthyl, or a hydrocarbon chain having 1 to 8 carbon atoms inclusive which is straight-chain or branched by a gem-dimethyl; and A-B represents: —(CH$_2$)$_2$—O—, —(CH$_2$)$_3$—O—, or —CO—CH=CH—, as well as their possible stereoisomers, epimers, and pharmaceutically-acceptable acid addition salts thereof; and medicinal products containing the same, useful in the treatment of a disorder requiring a 5-HT$_{1A}$ receptor antagonist.

15 Claims, No Drawings

OTHER PUBLICATIONS

Pharmacology 146, 253–259 (1988).

Millan, *Induction of Hypothermia as a Model of 5–Hydroxytryptamine$_{1A}$ Receptor–Mediated Activity in the Rat: A Pharmacological Characterization of the Actions of Novel Agonists and Antagonists,* Journal of Pharmacology and Experimental Therapeutics 264 No. 3, 1364–1376 (1993).

Millan, *5–Hydroxytryptamine (5–HT)$_{1A}$ Receptors and the Tail–Flick Response. I. 8–Hydroxy–2–(Di–n–Propylamino)Tetralin HBr–Induced Spontaneous Tail–Flicks in the Rat as an in vivo Model of 5–HT$_{1A}$ Receptor–Mediated Activity,* Journal of Pharmacology and Experimental Therapeutics 256 No. 3, 973–982 (1991).

Tricklebank, *Mediation of the Discriminative Stimulus Properties of 8–Hydroxy–2–(di–n–propylamino)tetralin (8–OH–DPAT) by the Putative 5–HT$_{1A}$ Receptor,* European Journal of Pharmacology 133, 47–56 (1987).

Eiden et al, *Arch. Pharm.* 322, pp. 589–592 (1989).

N-SUBSTITUTED N'-HETEROBICYCLIC PIPERAZINES HAVING PHARMACEUTICAL ACTIVITY

The present invention relates to new 1,4-disubstituted piperazines, a process for their preparation and pharmaceutical compositions containing them.

It relates especially to 1,4-disubstituted piperazines of formula I:

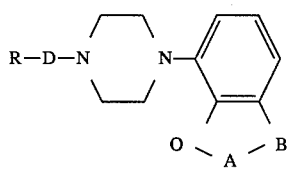

wherein:

R represents a radical of the formula:

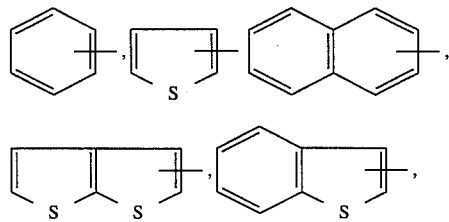

n being an integer 3 or 4 and

D represents a single bond or a hydrocarbon chain having from 1 to 8 carbon atoms which is straight-chain or branched by a gem-dimethyl, and —A—B— represents a radical of the formula:

$-(CH_2)_2-O-$, $-(CH_2)_3-O-$, $-CH=CH-$, $-CH_2-CH_2-$ or $-\underset{\underset{O}{\|}}{C}-CH=CH-$.

Some compounds of formula I include an asymmetrical carbon atom and as a result may be resolved into optical isomers, which are also included in the present invention.

The prior art closest to the present invention is illustrated by

PCT Specification No. 91/04250, which describes especially the product of formula:

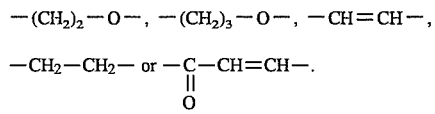

having antiarrhythmic properties, and

U.S. Pat. No. 4,335,126, which relates, inter alia, to the product of formula:

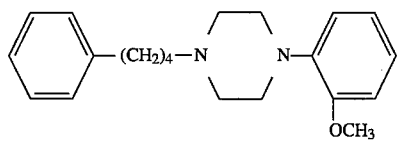

as an anti-aggressive agent.

None of those specifications either describes or suggests the compounds forming the subject of the present invention, which have a pharmacological activity of the HT1A antagonist type not exhibited by the prior art compounds mentioned above.

The present invention relates also to a process for the preparation of compounds of formula I which is characterised in that:

an N-monosubstituted piperazine of formula II:

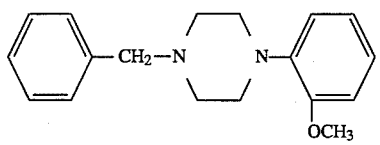

wherein the group —A—B— is as defined hereinbefore, is condensed either with:

a compound of formula III:

$$R-D-X \qquad (III)$$

wherein:

R and D are as defined hereinbefore and

X represents a halogen atom, or a mesyloxy or tosyloxy radical, or with:

a compound of formula IV:

$$R-D'-COOH \qquad (IV)$$

wherein

R is as defined hereinbefore; and

D' represents a single bond or a hydrocarbon chain having from 1 to 7 carbon atoms which is straightchain or branched by a gem-dimethyl; and the amide so obtained of formula V:

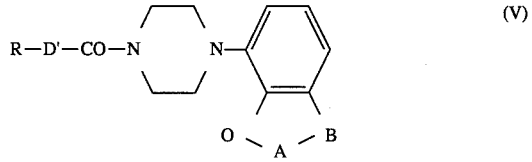

wherein R, D' and —A—B— are as defined hereinbefore, is reduced.

The condensation of compounds II and III is carried out especially advantageously in an appropriate solvent, such as, for example, acetone, methyl ethyl ketone, methyl isobutyl ketone, toluene, or dimethylformamide, in the presence of an acceptor for the acid formed during the course of the reaction, at a temperature of from 20 to 150° C. There may be used as acceptor, for example, an alkali metal carbonate, such as sodium carbonate, or a tertiary amine, such as triethylamine.

The condensation of compounds II and IV is carried out especially advantageously in an appropriate solvent such as, for example, methylene chloride, in the presence of carbonyl diimidazole.

The reduction of the amide V is advantageously carried out by means of lithium aluminium hydride, in an appropriate solvent, such as, for example, ether or tetrahydrofuran.

In addition, the amides of formula v are new intermediates which as such form part of the present invention.

The starting materials of formulae II, III and IV are either known products, or are products prepared from known compounds in accordance with known processes, as detailed hereinafter in the Examples.

The compounds of formula I yield salts with physiologically tolerable acids, which salts are also included in the present invention.

The compounds of the present invention have valuable pharmacological and therapeutic properties. Indeed pharmacological tests have demonstrated that the compounds of the invention behave in vitro and in vivo like very powerful and very selective $5HT_{1A}$ serotonin receptor ligands with an antagonistic activity towards that neurotransmitter at the level of the central nervous system, demonstrated by the pharmacological study exemplified hereinafter.

That activity enables the compounds of the present invention to be used in the treatment of disorders of the central nervous system, especially learning and memory disorders (Carli, M., and Samanin, R., Br. J. Pharmacol., 105, 720–726, 1992; Carli, M., Tranchina, S. and Samanin, R., Eur. J. Pharmacol., 211,227–234, 1992; Lister, R. G., $5HT_{1A}$ agonists, $5HT_3$ antagonists and benzodiazepines: their comparative behavioural pharmacology Ed. R. J. Rodgers and S. J. Cooper, Wiley & Son Ltd., Chichester, pp. 267–280, 1991), anxiety disorders (Barrett. J. E., and Gleeson, S. $5HT_{1A}$ agonists, $5HT_3$ antagonists and benzodiazepines: their comparative behavioural pharmacology Ed. R. J. Rodgers and S. J. Cooper, wiley & Son Ltd, Chichester, pp. 59–105, 1991; Glennon, R. A., Neurosci. & Behav. Rev. 14: 35–47, 1990; Lader, M. H., $5HT_{1A}$ agonists, $5HT_3$ antagonists and benzodiazepines: their comparative behavioural pharmacology Ed. R. J. Rodgers and S. J. Cooper, Wiley & Son Ltd, Chichester, pp. 343–363, 1991; Schweizer, E., and Rickels, K., $5HT_{1A}$ agonists, $5HT_3$ antagonists and benzodiazepines: their comparative behavioural pharmacology Ed. R. J. Rodgers and S. J. Cooper, Wiley & Son Ltd, Chichester, pp. 365–376, 1991; Taylor, D. P., and Moon, S. L., Neuropeptides, 19: 15–19, 1991; Treit, D., $5HT_{1A}$ agonists, $5HT_3$ antagonists and benzodiazepines: their comparative behavioural pharmacology Ed. R. J. Rodgers and S. J. Cooper, Wiley & Son Ltd, Chichester, pp. 107–131, 1991), depression (Cervo, L., Grignaschi, G. and Samanin, R. Eur. J. Pharmacol., 158: 53–59, 1988; Glennon, R. A. Neurosci. & Behav. Rev. 14: 35–47, 1990, Thiébot, M.-H. and Martin, P. $5HT_{1A}$ agonists, $5HT_3$ antagonists and benzodiazepines: their comparative behavioural pharmacology Ed. R. J. Rodgers and S. J. Cooper, Wiley & Son Ltd, Chichester, pp. 159–194, 1991), schizophrenia (Ahlenius, S., Pharmacol & Toxicol., 64: 3–5, 1989; Glennon, R. A., Neurosci. & Behav. Rev. 14: 35–47, 1990; Invernizzi, R. W., Cervo, L., and Samanin, R., Neuropharmacology, 27: 515–518, 1988), stress (Dourish, C. R., Hutson, P. H., and Ahlenius S., (Eds.) Brain $5HT_{1A}$ receptors, Chichester Press, Horwood, England, 1987; Fuller, R. W., Neuropsycho-pharmacology 3: 495–502, 1990; Glennon, R. A., Neurosci. & Behav. Rev. 14: 35–47, 1990), anorexia (Cooper, S. J., $5HT_{1A}$ agonists, $5HT_3$ antagonists and benzodiazepines: their comparative behavioural pharmacology Ed. R. J. Rodgers and S. J. Cooper, Wiley & Son Ltd, Chichester, pp. 233–265, 1991; Dourish, C. R., Hutson, P. H., and Ahlenius S., (Eds.) Brain $5HT_{1A}$ receptors, Chichester Press, Horwood, England, 1987), pain (Berge, O.G., Hole, K., and Dahle, H., Neurosci. Lett., 19: 219–223, 1980; Daval, G., Vergé, D., Basbaum, A. I., Bourgoin, S., and Hamon, M. Neurosci. Lett., 83: 71–76, 1987; Fasmer, O. B., Berge, O. G., Post, C. and Hole, K., Pharmacol. Biochem. Behav., 25: 883–888, 1986; Hamon, M., Collin, E., Chantrel, D., Daval, G., Vergé, D., Bourgoin, S. and Cesselin, F., Serotonin and Pain, ed. by J.-M. Besson, Elsevier, Amsterdam, pp. 53–72, 1990; Millan, M. J., Bervoets K. and Colpaert F. C., J. Pharmacol. Exp. Ther., 256: 973–982, 1991a; Millan, M. J., and Colpaert F. C., J. Pharmacol. Exp. Ther., 256: 983–992, 1991a; Millan, M. J. and Colpaert F. C., J. Pharmacol. Exp. Ther., 256: 993–1001, 1991b) and neuroendocrinal disorders such as diabetes (Chaouloff, F. and Jeanrenaud, B. J., Pharmacol. Exp. Ther., 243, 1159–1166, 1990; Schweizer, E. and Rickels, K., $5HT_{1A}$ agonists, $5HT_3$ antagonists and benzodiazepines: their comparative behavioural pharmacology Ed. R. J. Rodgers and S. J. Cooper, wiley & Son Ltd, Chichester, pp. 365–376, 1991; Taylor, D. P. and Moon, S. L., Neuropeptides, 19: 15–19, 1991). An involvement (for example hyperactivity) of $5HT_{1A}$ receptors was clearly demonstrated in these disorders (see references above). In addition, the effectiveness of the $5HT_{1A}$ ligand, buspirone, in the treatment of some of these disorders (for example anxiety) has been demonstrated in man (Goff, D. C., Midha, K. K., Brotman, A. W., McCormick, S., Waites, M. and Amico, E. T., J. Clin. Psychopharmacol., 11 : 193–197, 1991). The results obtained in the pharmacological study of the compounds of the present invention show without any ambiguity that the said compounds interact with $5HT_{1A}$ receptors in vitro and in vivo, and can therefore be used to treat the disorders mentioned above.

The present invention relates also to pharmaceutical compositions comprising as active ingredient a compound of formula I or a physiologically tolerable salt thereof, mixed with or in association with an appropriate pharmaceutical excipient, such as, for example, glucose, lactose, talcum, ethyl cellulose, magnesium stearate or cocoa butter.

The so-obtained pharmaceutical compositions are generally presented in dosage form and may contain from 0.1 to 100 mg of active ingredient. They may, for example, be in the form of tablets, dragees, gelatin capsules, suppositories or injectable or drinkable solutions and, depending on the case in question, may be administered by the oral, rectal or parenteral route at a dose of from 0.1 to 100 mg of active ingredient from 1 to 3 times per day.

The following Examples illustrate the invention; the melting points are determined using a Kofler hot plate (K) optionally using a microscope (M.K.).

EXAMPLE 1

4-(Benzodioxan-5-yl)-1-[3-(thiophen-3-yl)propyl]piperazine

Step 1

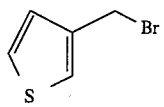

7.05 ml (75.0 mmol) of phosphorus tribromide are poured dropwise over a period of 20 minutes onto 25.4 g (222.5 mmol) of thien-3-ylmethanol dissolved in 45 ml of benzene at about 2°–3° C. The whole is stirred for 1 hour at that temperature and then for 4 hours at room temperature. The reaction mixture is poured into a mixture of ice and water and is then extracted with ether. The combined ethereal phases are washed with water. After drying over magnesium sulphate and concentrating, followed by distillation using a Kugelrohr (b.p.: 40°–80° C. at 1866 to 1999 Pa), 30.2 g of the desired brominated compound are obtained (yield: 77 %).

Step 2

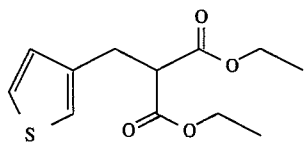

29.0 g (181.2 mmol) of diethyl malonate are poured dropwise at room temperature, over a period of 15 minutes, onto a solution of sodium ethoxide prepared from 4.17 g (181.2 m.atm.g) of sodium and 100 ml of anhydrous ethanol. Stirring is continued for 1 hour at room temperature, then the brominated compound prepared in Step 1 is added dropwise over a period of 1 hour 15 minutes whilst maintaining the temperature at about 16° C. Stirring is continued for a further hour at room temperature and then for one hour at reflux. The mixture is evaporated to dryness and the residue is taken up with water and extracted with ether. After drying over magnesium sulphate and concentrating, followed by distillation using a Kugelrohr (b.p. : 50°–100 ° C. at 6,664 Pa), 28.6 g of the diester are obtained (yield: 66%).

Step 3

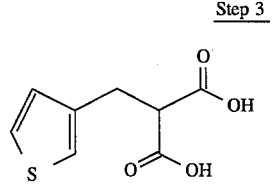

24.8 g (441.6 mmol) of potassium hydroxide in 25 ml of water are added at room temperature to 28.3 g (110.4 mmol) of the diester obtained in the preceding Step in 55 ml of ethanol and the whole is then refluxed for 7 hours. After evaporation to dryness, the residue is taken up with water and slowly poured into 90 ml of 6N hydrochloric acid. The mixture is extracted with ethyl acetate. The combined organic phases are washed with a saturated aqueous solution of sodium chloride and, after drying over magnesium sulphate and concentrating, 20.4 g of the diacid are obtained (yield: 92 %). M.p. (K): 138° C.

Step 4

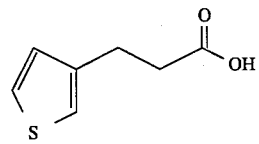

20.3 g (101.4 mmol) of the diacid obtained in the preceding Step are dissolved in 100 ml of N,N-dimethylacetamide and the whole is then refluxed for 1 hour. After evaporation of the solvent, the residue is taken up with ether and washed with water. After drying over magnesium sulphate and concentrating, 14.2 g of the desired acid are obtained (yield: 90 %). M.p. (K): about 50° C.

Step 5

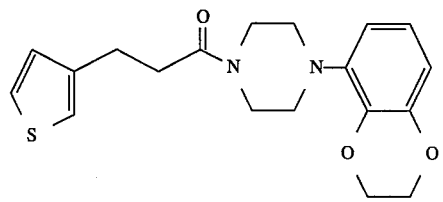

3.41 g (21.0 mmol) of carbonyl diimidazole are added at room temperature in one batch to 3.13 g (20.0 mmol) of the acid obtained in the preceding Step in 40 ml of methylene chloride. The whole is maintained at room temperature for 7 hours with stirring, then a solution of 4.4 g (20 mmol ) of N-(benzodioxan-5-yl)-piperazine in 25 ml of methylene chloride is added. The whole is then again maintained at room temperature overnight with stirring, after which methylene chloride is added and the whole is washed with N sodium hydroxide solution and then with water. After drying over magnesium sulphate and concentrating, 7.4 g of the desired amide are obtained in the form of an oil (quantitative yield).

Step 6

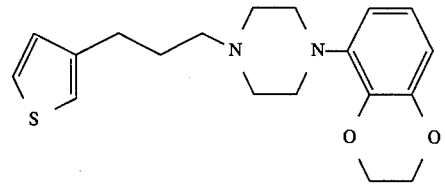

7.4 g (20.0 mmol) of the amide obtained in the preceding Step in 130 ml of THF are added dropwise over a period of 1 hour 10 minutes to 0.76 g (20.0 mmol) of lithium aluminium hydride in 40 ml of THF at room temperature. The whole is maintained at room temperature overnight with stirring, then hydrolysed at 0° C. with 0.53 ml of water, then with 0.42 ml of 20 % sodium hydroxide, then with 1.9 ml of water. The resulting salts are filtered through a frit. After drying over magnesium sulphate and concentrating, 7.0 g of crude product are obtained. The product is dissolved in 100 ml of ethanol and then treated with 2.2 equivalents of ethereal hydrogen chloride.

After evaporation to dryness and recrystallisation from 40 ml of ethanol, 5.1 g of the impure dihydrochloride are obtained.

After rendering basic (4.2 g) and recrystallisation from 21 ml of diisopropyl ether, 2.5 g of 4-(benzodioxan-5-yl)-1-[3-(thiophen-3-yl)propyl]-piperazine are obtained ((yield: 32 %).

M.p. (K): 71°–73° C.

NMR: $^1$H (CDCl$_3$/TMS): 7.25 (m, 1H); 6.95 (m, 2H); 6.75 (t, 1H); 6.55 (m, 2H); 4.25 (m, 4H); 3.10 (m, 4H); 2.75 (m, 6H); 2.45 (m, 2H); 1.85 (m, 2H).

EXAMPLE 2

(R,S)-4-(benzodioxan-5-yl)-1-[(4,5,6,7-tetrahydrobenzo[b]thiophen- 5-yl)methyl]piperazine and its dihydrochloride Step 1

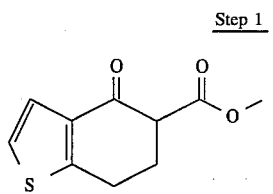

16.6 g (465 mmol) of 60 % sodium hydride are added in portions over a period of 10 minutes to 23.6 g (155 mmol) of 4-oxocyclohexa[ b]thiophene (commercial product) in 475 ml of dimethyl carbonate at 0° C. The whole is refluxed for 3 hours with vigorous stirring, allowed to cool, and poured onto 1 1 of a mixture of ice and water containing 45 ml of acetic acid. Extraction is carried out with ether. After drying over magnesium sulphate and concentrating, followed by recrystallisation from 150 ml of diisopropyl ether, 20.4 g of the desired keto ester are obtained (yield: 94%).

M.p. (K): 88° C.

Step 2

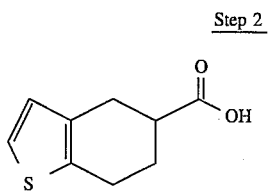

Zinc amalgam is prepared from 69.1 g of zinc, 6.9 g of mercuric chloride, 3.2 ml of concentrated hydrochloric acid and 103 ml of water. After having decanted off the aqueous phase, 55 ml of water, 116 ml of concentrated hydrochloric acid and 30.4 g (144.6 mmol) of the keto ester obtained in the preceding Step in 72 ml of toluene are added. The whole is refluxed for 2 hours and then allowed to cool, and the phases are separated. The aqueous phase is reextracted with toluene. The combined toluene phases are extracted with a saturated aqueous sodium hydrogen carbonate solution and then washed with water. After drying over magnesium sulphate and concentrating, followed by distillation using a Kugelrohr (b.p.: 55°–75° C. at 40 Pa), 20.5 g of the methyl ester corresponding to the desired acid are obtained (yield: 78%).

The aqueous sodium hydrogen carbonate phases are combined and poured dropwise at 0° C. onto a 6N hydrochloric acid solution. The resulting precipitate is filtered and washed with water. After drying in air, 2.25 g of the desired acid are obtained (yield: 8%).

M.p. (K): 115° C.

Step 3

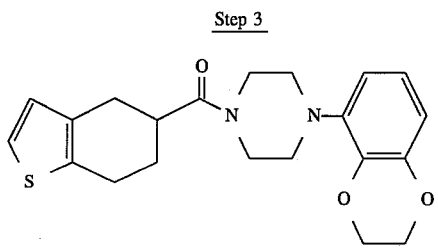

The procedure is as in Example 1, Step 5, starting from 2.3 g (12.6 mmol) of the acid obtained in the preceding Step and 2.8 g (12.6 mmol ) of N- (benzodioxan-5-yl)piperazine. 4.8 g of the desired amide are obtained in the form of a meringue (quantitative yield).

Step 4

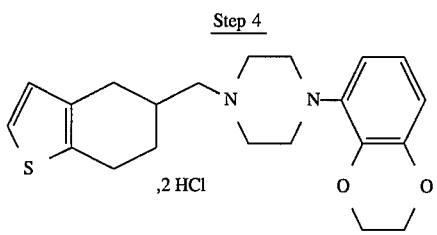

The procedure is as in Example 1, Step 6, starting from 4.6 g of the amide obtained in the preceding Step. The crude product obtained,.(R,S)-4-(benzodioxan-5-yl)-1-[ (4,5,6,7-tetrahydrobenzo[b]thiophen-5-yl)methyl]piperazine is chromatographed on silica (eluant: dichloromethane/methanol 97/3), then dissolved in 100 ml of ethanol and treated with 2.2 equivalents of ethereal hydrogen chloride. After evaporation to dryness and recrystallisation from 70 ml of ethanol, 3.0 g of (R,S)- 4-(benzodioxan-5-yl)-1-[(4,5,6,7-tetrahydrobenzo[b]thio are obtained phen-5-yl)methyl ]piperazine dihydrochloride (yield: 56% ).

M.p. (MK) : 213°–217° C. (sublimation towards 180° C.).

NMR: $^1$H (CDCl$_3$/TMS): 7.65 (1H); 7.05 (d, 1H); 6.85 to 7.0 (m, 2H); 6.8 (d, 1H); 5.15 (m, 2H); 4.2 to 4.6 (m, 6H); 3.65 (m, 4H); 2.75 to 3.3 (m, 5H); 2.25 to 2.7 (m, 3H); 1.75 (m, 1H); 13.4 (s, broad, exchangeable with D$_2$O).

EXAMPLE 3

(R,S)-4-(benzodioxan-5-yl)-1-[ (cyclopenta[b]thiophen-5-yl)methyl]piperazine

Step 1

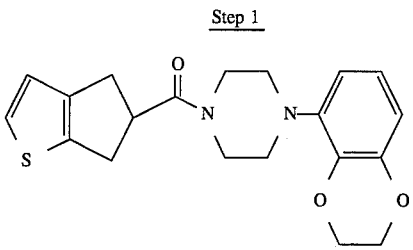

The procedure is as in Example 1, Step 5, starting from 2.6 g (11.9 mmol) of N-(benzodioxan-5-yl)-piperazine and 2.0 g (11.9 mmol) of cyclopenta[b]thiophene-5-carboxylic acid, itself obtained as described in Example 2, Steps 1 and 2, from 6-oxocyclopenta[b]thiophene (the synthesis of which is described in: J. Pharm. Sciences 1963, 52, 898). 3.7 g of the amide are obtained in the form of a meringue (yield: 84%), after filtration of the crude product on silica (eluant: dichloromethane/methanol 97.5/2.5).

Step 2

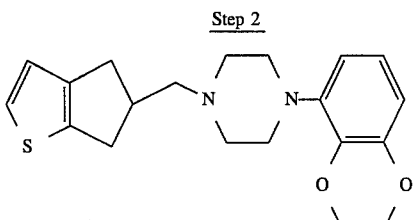

The procedure is as in Example 1, Step 6, starting from 3.6 g of the amide obtained in the preceding Step. The crude product obtained is chromatographed on silica (eluant: ethyl acetate), then dissolved in 50 ml of ethanol and treated with 2.2 equivalents of ethereal hydrogen chloride. The dihydrochloride obtained is purified by rendering basic and recrystallising from 35 ml of diisopropyl ether; 0.60 g of (R,S)-4-(benzodioxan-5-yl)-1-[(cyclopenta[b]thiophen-5-yl)methyl]piperazine (free base) is obtained (yield: 17%).

M.p. (MK): 146°–147° C.

NMR: $^1$H (CDCl$_3$/TMS): 7.15 (d, 1H); 6.75 (m, 2H); 6.55 (m, 2H); 4.25 (m, 4H); 2.8 to 3.3 (m, 7H); 2.4 to 2.75 (m, 8H).

EXAMPLE 4

4-(Benzodioxan-5-yl)-1-[4-(thiophen-3-yl)butyl]piperazine and its dihydrochloride

Step 1

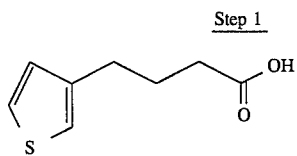

The 4-(3-thienyl)butanoic acid was obtained by malonic synthesis from 2-(3-thienyl)bromoethane in accordance with the methods described in Example 1, Steps 1, 2, 3 and 4.

Step 2

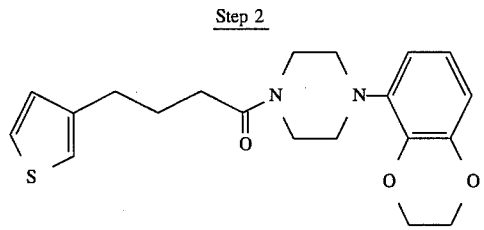

The procedure is as in Example 1, Step 5, starting from 2.06 g (12.1 mmol) of the acid obtained in the preceding Step. 4.4 g of the desired amide are obtained (yield: 98%).

Step 3

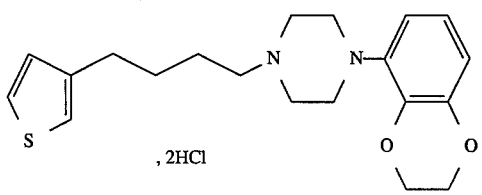

The procedure is as in Example 1, Step 6, starting from 4.3 g (11.5 mmol) of the amide obtained in the preceding Step. After reaction, the 4-(benzodioxan-5-yl)-1-[4-(thiopheny-3-yl)butyl]piperazine obtained is chromatographed on silica (eluant: dichloromethane/methanol 98/2), then dissolved in 50 ml of methanol and treated with 7.8 ml (2.2 equivalents) of 2.3N ethereal hydrogen chloride. Evaporation and recrystallisation from 15 ml of methanol yields 2.1 g of the dihydrochloride of 4-(benzodioxan-5-yl)-1-[4-(thiopheny-3-yl)butyl]piperazine, m.p. (M.K.): 210°–217° C. (yield: 42%).

EXAMPLE 5

4-(Benzodioxan-5-yl)-1-[2-(naphth-1-yl)ethyl]piperazine and its monohydrochloride

Step 1

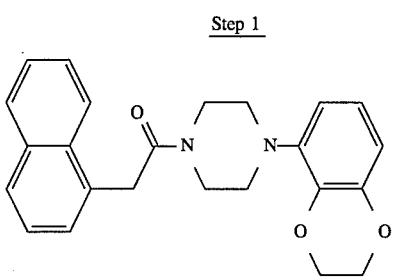

The procedure is as in Example 1, Step 5, starting from 1.86 g (10.0 mmol) of commercial α-naphthylacetic acid. 3.45 g of the desired amide are obtained (yield: 89%).

Step 2

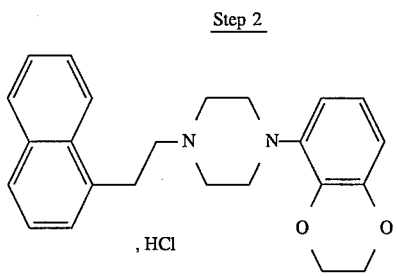

The procedure is as in Example 1, Step 6, starting from 3.4 g (8.7 mmols of the amide obtained in the preceding Step. After reaction, the product obtained is dissolved in 50 ml of methanol and then treated with 8.7 ml of 2.1N ethereal hydrogen chloride. Evaporation and recrystallisation from 75 ml of methanol yields 1.55 g of the monohydrochloride of 4-(benzodioxan-5-yl)-1-[2-(naphth-1-yl)ethyl] piperazine, m.p. (M.K.) : 255°–260° C. (yield: 43%).

EXAMPLE 6

4-(Benzodioxan-5-yl)-1-[2-(naphth-2-yl)ethyl]piperazine and its monohydrochloride

Step 1

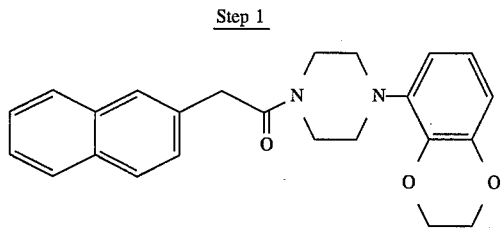

The procedure is as in Example 1, Step 5, starting from 1.86 g (10.0 mmol) of commercial β-naphthylacetic acid. 3.55 g of the amide are obtained (yield: 91%).

Step 2

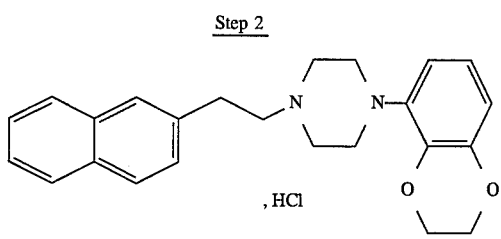

The procedure is as in Example 1, Step 6, starting from 3.3 g (8.5 mmol) of the amide obtained in the preceding Step. After reaction, the product obtained is recrystallised from 40 ml of diisopropyl ether, then dissolved in 50 ml of methanol and subsequently treated with 4.6 ml of 2.1N ethereal hydrogen chloride. Evaporation and recrystallisation twice from methanol yields 1.05 g of the monohydrochloride of 4-(benzodioxan-5-yl)-1-[2-(naphth-2-yl)ethyl] piperazine, m.p. (M.K.) : 249°–263° C. (yield: 30%).

EXAMPLE 7

4-(Benzodioxan-5-yl)-1-[2-(benzo[b]thiophen-3-yl)ethyl]piperazine and its monohydrochloride

Step 1

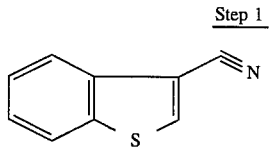

20 ml of a 50% 3-chloromethylbenzo[b]thiophene solution in toluene (55.0 mmol) in 20 ml of DMSO are added at room temperature, over a period of 1 hour, to 3.23 g (66.0 mmol) of finely ground sodium cyanide suspended in 10 ml of DMSO. The whole is stirred for 24 hours at room temperature and is then poured into iced water and extracted with ether. The combined ethereal phases are washed with water. Drying over magnesium sulphate followed by concentration yields 9.35 g of the nitrile (quantitative yield).

Step 2

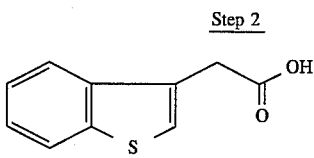

10.7 g (190 mmol) of potassium hydroxide are dissolved in 5 ml of water and then 9.2 g (53.1 mmol) of the nitrile obtained in the preceding Step in 30 ml of ethanol are added thereto. The whole is refluxed for 7 hours and is then evaporated to dryness, taken up in water and washed with ethyl acetate. The aqueous phase is then poured into 60 ml of 4N hydrochloric acid, and the solid formed is filtered, rinsed with water and dried in vacuo to yield 8.0 g of the desired acid, m.p. (K) : 111° C. (yield: 78%).

Step 3

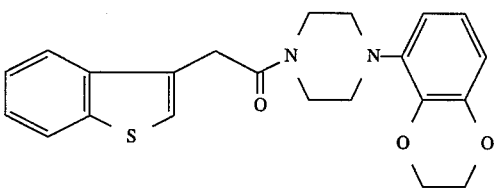

The procedure is as in Example 1, Step 5, starting from 1.92 g (10.0 mmol) of the acid obtained in the preceding Step. 3.6 g of the desired amide are obtained (yield: 91%).

Step 4

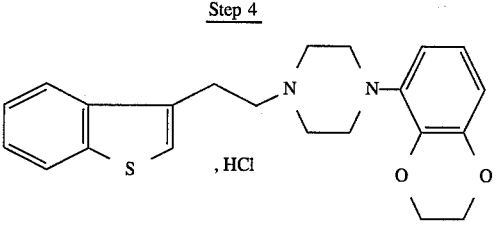

The procedure is as in Example 1, Step 6, starting from 3.5 g (8.9 mmol) of the amide obtained in the preceding Step. After reaction, the product obtained is chromatographed on silica (eluant: ethyl acetate), dissolved in 50 ml of methanol and treated with 3.3 ml of 2.2N ethereal hydrogen chloride. Evaporation and recrystallisation from 40 ml of methanol yields 0.92 g of the monohydrochloride of 4-(benzodioxan-5-yl)-1-[2-(benzo[b]thiophen-3-yl)ethyl]piperazine, m.p. (M.K.) : 244°– 251° C. (yield: 25%).

EXAMPLE 8

4-(Benzodioxan-5-yl)-1-[2-(thieno[2,3-b]thiophen-2-yl)ethyl]piperazine

Step 1

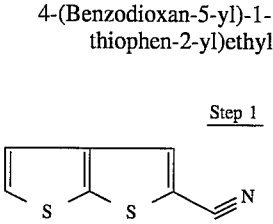

2.6 ml (36.2 mmol) of thionyl chloride are added dropwise at 0° C., over a period of 15 minutes, to 5.6 g (32.9 mmol) of 2-hydroxymethylthieno[2,3-b]thiophene (the synthesis of which is described in J. Med. Chem. 1991, 34(6), 1805–1817) and 2.7 ml (32.9 mmol) of pyridine in 66 ml of chloroform. The whole is stirred for 2 hours at room temperature and then for 15 minutes at reflux, and is then cooled, washed with water and dried for several minutes over magnesium sulphate before effecting a solvent exchange with toluene. The toluene solution is added dropwise at room temperature over a period of 55 minutes to 3.22 g (65.8 mmol) of finely ground sodium cyanide suspended in 40 ml of DMSO. The whole is stirred for 3 days at that temperature and then poured into water and extracted with ether. The combined ethereal phases are washed with water, dried over magnesium sulphate and concentrated to yield 4.6 g of the desired nitrile, m.p. (K): 56° C. (yield: 78%).

Step 2

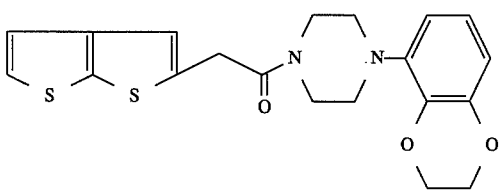

The procedure is as in Step 2 of Example 7, starting from 4.5 g (25.1 mmol) of the nitrile of Step 1 above, and yields 3.8 g of the desired acid, m.p. (K) : 138° C. (yield: 76%).

Step 3

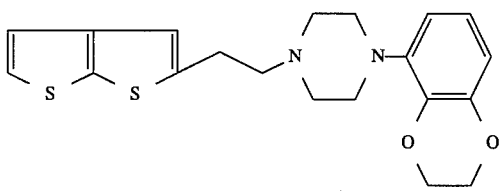

The procedure is as in Example 1, Step 5, starting from 3.75 g (18.9 mmol) of the acid obtained in the preceding Step. Chromatography on silica (eluant: dichloromethane/methanol 97/3) yields 5.55 g of the desired amide (yield: 73%).

Step 4

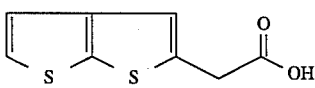

The procedure is as in Example 1, Step 6, starting from 5.5 g (13.7 mmol) of the amide obtained in the preceding Step. After reaction, the product obtained is chromatographed on silica (eluant: dichloromethane/ethyl acetate 50/50), then recrystallised from 50 ml of methanol and subsequently from 10 ml of acetonitrile to yield 0.90 g of 4-(benzodioxan-5-yl)-1-[2-(thieno[2,3-b]thiophen-2yl)ethyl] piperazine, m.p. (M.K.) : 120°–122° C. (yield: 17%).

EXAMPLE 9

4-(Benzodioxan-5-yl)-1-<[2,2-dimethyl-3-(thiophen-3-yl)]propyl)piperazine and its dihydrochloride Step 1

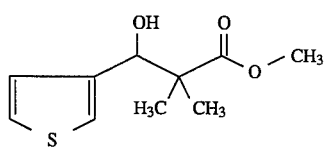

20.9 g (110 mmol) of titanium tetrachloride in 220 ml of dichloromethane are added at −78° C., over a period of 30 minutes, to 11.2 g (100 mmol) of thiophene-3-carboxaldehyde in 800 ml of dichloromethane. The whole is stirred at −78° C. for 15 minutes and then, over a period of 5 minutes, 19.2 g (110 mmol) of 2-methyl-1-methoxy-1-trimethylsilyloxypropene in 120 ml of dichloromethane are added. After 2 hours at −78° C., then 2 hours at towards −60° C., the whole is hydrolysed at −78° C. with 600 ml of a 10% aqueous potassium carbonate solution. The whole is allowed to return to room temperature, then the phases are separated and the aqueous phase is reextracted with dichloromethane. The combined organic phases are washed with water and dried over magnesium sulphate. After evaporation and solidification in hexane, 10.7 g of the desired hydroxy ester are obtained, m.p. (K) : 66° C. (yield: 50%).

Step 2

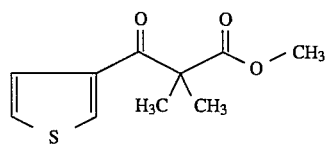

In portions 11.0 g (37.4 mmol) of potassium dichromate, then 6.4 g (29.9 mmol) of the hydroxy ester obtained in the preceding Step, are added at 0° C. to 5.1 ml of concentrated sulphuric acid in 60 ml of water. The whole is allowed to return to room temperature and stirred for 4 hours. Extraction is then carried out with ether, and the combined ethereal phases are washed with water until neutral and dried over magnesium sulphate. Evaporation and chromatography on silica (eluant: dichloromethane/ethyl acetate 97/3) yields 3.15 g of the desired keto ester in the form of an oil (yield: 50%).

Step 3

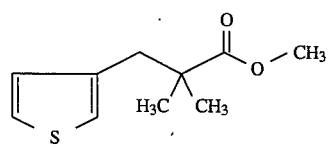

0.68 g (2.5 mmol) of mercuric chloride and 6.8 g (103 mmol) of intimately ground zinc powder are stirred for 15 minutes in 10 ml of water containing 0.31 ml of concentrated hydrochloric acid. The liquid phase is removed and 5.6 ml of water and 11.3 ml of concentrated hydrochloric acid are added to the amalgam, followed by 3.0 g (14.1 mmol) of the keto ester obtained in the preceding Step in 10 ml of toluene. The whole is stirred vigorously at reflux for 7 hours, then cooled, and the amalgam is removed. The phases are separated and the aqueous phase is reextracted with toluene. The combined toluene phases are washed with a saturated aqueous solution of sodium hydrogen carbonate, then with water, and dried over magnesium sulphate. Evaporation and chromatography on silica (eluant: dichloromethane) yields 2.0 g of the desired ester in the form of oil (yield: 71%).

Step 4

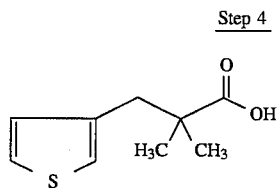

1.9 g (9.6 mmol) of the ester obtained in the preceding Step in 10 ml of methanol and 10 ml of N sodium hydroxide solution are stirred for 23 hours at room temperature. The whole is evaporated to dryness, then taken up in 20 ml of N hydrochloric acid and extracted with ethyl acetate. The combined organic phases are washed with a saturated aqueous solution of sodium chloride and dried over magnesium sulphate. Evaporation yields 1.68 g of the desired acid, m.p. (K) : 56° C. (yield: 95%).

Step 5

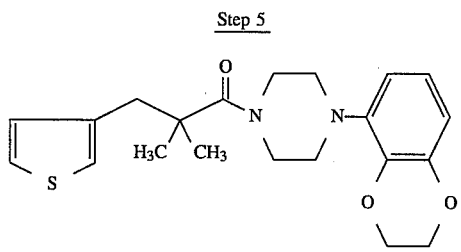

The procedure is as in Example 1, Step 5, starting from 1.55 g (8.4 mmol) of the acid obtained in the preceding Step. Chromatography on silica (eluant: dichloromethane/methanol 97/3) yields 1.3 g of the desired amide (yield: 40% ).

Step 6

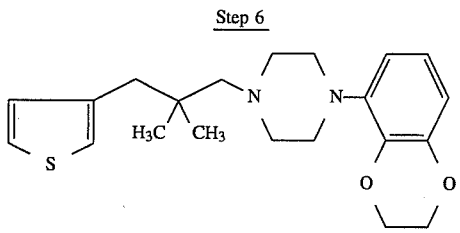

The procedure is as in Example 1, Step 6, starting from 1.22 g (3.2 mmol) of the amide obtained in the preceding Step. After reaction, the product obtained is chromatographed on silica (eluant: dichloromethane/ethyl acetate 50/50), then solidified in 15 ml of acetonitrile to yield 0.19 g of the dihydrochloride of 4-(benzodioxan-5-yl)-1-([ 2,2-dimethyl-3-(thiophen-3-yl)]propyl)piperazine, m.p. (M.K.) : 201°–203° C.

EXAMPLE 10

4-(Benzodioxan-5-yl)-1-[(thiophen-3-yl) methyl] piperazine and its dihydrochloride

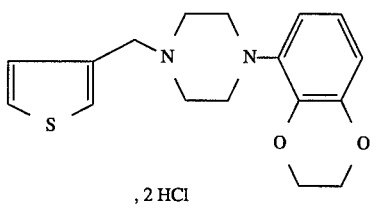

, 2 HCl 1.15 g (6.5 mmol) of (3-thienyl)methane bromide (obtained in Example 1, Step 1), 1.6 g (6.2 mmol) of the monohydrochloride of 4-(benzodioxan-5-yl)piperazine and 2.63 g (24.8 mmol) of sodium carbonate in 25 ml of methyl isobutyl ketone are mixed at room temperature. The mixture is refluxed for 20 hours, then evaporated to dryness, taken up in ethyl acetate and washed with N sodium hydroxide solution then with a saturated aqueous solution of sodium chloride, and subsequently dried over magnesium sulphate. After evaporation followed by chromatography on silica (eluant: dichloromethane/methanol 97/3), the residue, 4-(benzodioxan-5-yl)-1[ (thiophen-3-yl)methyl]piperazine, (1.7 g), is dissolved in 25 ml of ethanol and treated with 5.2 ml (2.2 equivalents) of 2.3N ethereal hydrogen chloride. The whole is evaporated to dryness and then recrystallised from 30 ml of ethanol to yield 1.22 g of the dihydrochloride of 4-(benzodioxan- 5-yl)-1-[(thiophen-3-yl)methyl]piperazine, m.p. (M.K.): 218°–223° C. (yield: 62%).

EXAMPLE 11

4-(Benzodioxan-5-yl)-1-[2-(thiophen-3-yl) ethyl]piperazine

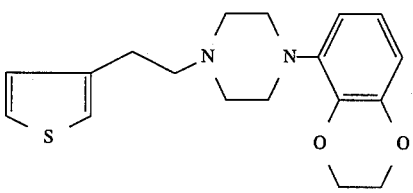

The procedure is as in Example 10, starting from 1.37 g (6.5 mmol) of 1-bromo-2-(3-thienyl)ethane (obtained from commercial 2-(3-thienyl)ethanol by the method of Example 1, Step 1). After reaction, the product obtained is recrystallised from 25 ml of diisopropyl ether to yield 1.25 g of 4-(benzodioxan-5-yl)-1-[2-(thiophen-3-yl)ethyl] piperazine, m.p. (M.K.) : 100°–102° C. (yield: 61%).

EXAMPLE 12

4-(Benzodioxan-5-yl)-1-(3-phenylpropyl)piperazine and its dihydrochloride

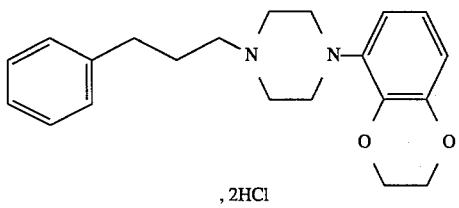

, 2HCl

The procedure is as in Example 10, starting from 0.91 ml (6.0 mmol) of commercial 1-bromo-3-phenylpropane. After reaction and chromatography on silica (eluant: dichloromethane/methanol 97/3), the residue, 4-(benzodioxan-5-yl)-1-(3-phenylpropyl)piperazine (1.7 g), is dissolved in 25 ml of ethanol and treated with 4.8 ml of 2.3N ethereal hydrogen chloride. The whole is evaporated to dryness and then recrystallised from 20 ml of ethanol to yield 1.47 g of the dihydrochloride of 4-(benzodioxan-5-yl)-1(3-phenylpropyl)piperazine, m.p. (M.K.) : 200°–203° C. (yield: 75%).

EXAMPLE 13

4-(Benzodioxan-5-yl)-1-[2-(thiophen-2-yl)ethyl]piperazine and its monohydrochloride

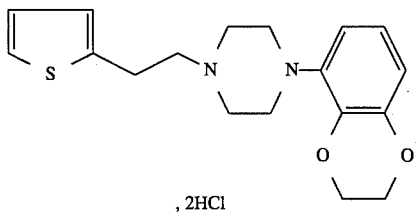

, 2HCl

The procedure is as in Example 10, starting from 2.53 g (12.0 mmol) of 1-bromo-2-(2-thienyl)ethane (obtained from commercial 2-(2-thienyl)ethanol by the method of Example 1, Step 1). After reaction, the residue, 4-(benzodioxan-5-yl)-1-[2-(thiophen-2-yl)ethyl]piperazine (2.85 g), is dissolved in 50 ml of methanol and then treated with 4.9 ml of 2.1N ethereal hydrogen chloride. The whole is evaporated to dryness and then recrystallised from 35 ml of ethanol to yield 2.4 g of the monohydrochloride of 4-(benzodioxan-5-yl)-1-[2-(thiophen-2-yl)ethyl]piperazine, m.p. (M.K.): 235°–240° C. (yield: 60%).

EXAMPLE 14

PHARMACOLOGICAL STUDY The compounds of the present invention were studied in comparison with buspirone, a reference product known as a $HT_{1A}$ serotoninergic receptor ligand.

A) Methodology

The tests were carried out using male Wistar rats weighing 200 to 220 g having free access to their food and to their drinking water in standard cages.

The animals are isolated individually for the tests for hypothermia, corticosterone secretion and flat body posture, or combined in groups of three for the tailflick test.

The temperature of the laboratory is maintained at 21°±1° C. and a humidity of 60±5%. They are subjected to a light/darkness cycle of 12 hours/12 hours (the light cycle beginning at 7.30 in the morning).

1) In vitro study—binding test

The hippocampus of the brains of decapitated rats was immediately frozen on solid carbon dioxide and then kept at −80° C. until preparation of the membranes. The tissue was homogenised at 4° C. in the appropriate buffer using a Polytron (Brinkman Instruments, Lucerne, Switzerland) and centrifuged at 20,000 revs/min.

Incubation was carried out for 30 minutes at 25° C. Non-specific binding was established by 10 μmol of 5HT. The tests were terminated by rapid filtration using a Brandel harvester through glass fibre filters pretreated with 0.1% polyethylene imine.

For each cold ligand, a minimum of 3 values was considered, producing an inhibition of between 20 and 80% of the binding of the hot ligand. The $IC_{50}$ values were determined in accordance with process 8 of Tallarida R. J. and Murray R. B., Manual of Pharmacological calculations with computer programs, Springer Verlag, New York, (1987).

The pKi was calculated in accordance with the following formula:

$$pKi = -\log\left(\frac{IC_{50}}{1 + [L]/Kd}\right)$$

wherein [L] is the concentration of the hot ligand ($[^3]H$-8-OH-DPAT, 0.4 nM) and Kd is the apparent dissociation constant determined from the saturation experiments.

The substances studied were dissolved in the incubation buffer.

2) In vivo study a/ General procedure regarding tests for agonist and antagonist activities towards $5HT_{1A}$ receptors.

The compounds to be studied were administered by the subcutaneous route (s.c.) 60 minutes before the beginning of the test, that is to say 30 minutes before the solvent (agonist responses) or the 8-OH-DPAT (antagonist responses).

In all of the tests the solvent is used in parallel as a control. The animals were left to rest in their cage during the period between the injections and the evaluation. For the agonist studies, the solvent was administered at 1 ml/kg s.c. 30 minutes before the beginning of the test. For the antagonist studies, doses of 8-OH-DPAT that induce sub-maximal responses were chosen, that is doses of 0.63, 0.16, 0.16 and 0.16 mg/kg s.c. for, respectively, the tail flick test, flat body posture test, corticosterone secretion test and hypothermia test.

b/ Flat body posture (or FBP) and secretion of corticosterone (CS).

The same animals were used to evaluate the influence of the compounds studied on FBP and on the determination of the plasma concentration of CS. All of the tests were carried out in the morning between 10.30 and 12.300 that is to say when the circadian levels of CS are lowest.

25 minutes after the treatment (that is to say 5 minutes before decapitation) the animals are observed in their cages and the presence or absence of FBP is noted.

The presence of FBP is defined by a characteristic posture of the animal. That posture is in the ventral decubitus position with the posterior limbs clearly extended. 5 minutes after the observation of FBP, the animals are decapitated and the blood from the trunk is collected in cooled tubes containing 50 μl of a 10% EDTA solution. After centrifugation at 4000 revs/min, the plasma is removed and stored at −30° C. until determination.

The CS was determined by a radio-competitive determination for a plasma protein that binds the CS: transcortine. The latter is obtained from a monkey serum. The separation of the CS-transcortine complexes from the free CS was carried out by means of a solution of dextran and active carbon. The detection limit was 50 pg/tube. The intra- and inter-experiment variations in determination were 5 and 15% respectively [cf Rivet J. M. et al, Eur. J. Pharmacol., 183,634–635 (1990)].

The CS base rates in the plasma never being zero, the following formula was used to calculated the percentage inhibition of plasma CS induced by 8-OH-DPAT:

$$\% \text{ inhibition} = 100 \times \frac{(\text{antagonist} + \text{agonist}) - \text{antagonist alone}}{(\text{solvent} + \text{agonist}) - \text{solvent alone}}$$

c/ Body temperature (BT)

The rats are immobilised and a lubricated digital thermometer (Termistroprobe of Testotherm, Basle, Switzerland) is inserted into the rectum to a depth of 5 cm. 30 seconds after insertion, the temperature is read on a digital scale. The percentage inhibition is calculated using the formula given above.

d/ Spontaneous tail flick (STF) test:

The tail flicks were determined on the animals in horizontal opaque plastics cylinders with the tail of the animals hanging freely on the edge of the laboratory work bench. After allowing 5 minutes for adaptation, the number of movements made in 5 minutes was recorded. An STF is defined as being an elevation of the tail to a level higher than that of the axis of the body [Millan M. J. et al., J. Pharmacol. Exp. Ther., 256, 973–982 (1990)].

e/ Drug discrimination (DD)

Male rats are maintained at 85% of their normal body weight by means of food restriction. In soundproofed chambers the animals are trained to press a pedal to obtain food according to an FR10 procedure (Fixed Ratio 10; the food is supplied to the rat when it has pressed the lever 10 times).

Learning or training

Daily sessions of 15 minutes are preceded by an injection of solvent or of the training drug (0.31 mg/kg of 8-OH-DPAT, j.p.). The animal receives a pellet of food after pressing 10 times on the "solvent" or "drug" pedal according to the compound administered before the session.

Drug discrimination test

After the learning period the animals are tested twice a week (Wednesday and Friday). On the other three days training sessions are carried out.

On the training days the rats are given either solvent or 8-OH-DPAT 15 minutes before being tested.

On the test days the rats receive the chemical substance 60 minutes before the session.

The capacity of the chemical substance administered to induce a response (pressing on the "solvent" or "drug" (8-OH-DPAT) lever) is recorded.

7 animals chosen at random are used for each substance and for each dose. During the test period, the lever on which the rat first presses 10 times is determined as the lever chosen—a food pellet is then delivered. That selected lever will be reinforced by the delivery of food up to the end of the test session. The percentage of animals selecting the "drug" lever at a particular dose is calculated. In addition, the total number of responses carried out on the two levers is expressed as a percentage of the number of responses carried out on the "solvent" lever obtained on the occasion of a preceding training session.

f/ Analysis of the in vivo results

In general, after variance analysis, the results are subjected to the Dunett test. The results are taken as significant if $p < 0.05$.

For analysis of the dose-response curves concerning the induction of STF, CS and hypothermia, the minimum effective dose (MED) in mg/kg was determined, that is to say the dose which induces a response significantly different from that produced by the solvent.

For the analysis of the dose-response curves concerning the inhibition of STF, CS and hypothermia, the $ID_{50}$ values—in mg/kg (dose reducing the action of 8-OH-DPAT by 50%) were calculated as well as the 95% confidence limits using a method inspired by the Finney method (1964).

For the dose-response for the induction and inhibition of FBP, the $ED_{50}$ values (doses at which 50% of the animals show a response) were calculated by the Litchfield and Wilcoxon method.

g/ Compounds studied

The doses of the compounds tested are all expressed in base terms. Unless specified otherwise, all of the compounds were dissolved in sterile water (to which if necessary a few drops of lactic acid were added) and administered at a volume of 1 ml/kg s.c.

B) Results

The results are listed in Tables 1 and 2 below.

TABLE 1

| Binding of $5HT_{1A}$ receptors | |
|---|---|
| MOLECULE | AFFINITY (pKi) |
| Reference product BUSPIRONE | 7.93 |
| Example 1 | 8.76 |
| Example 3 | 8.77 |
| Example 4 | 9.42 |
| Example 5 | 8.89 |
| Example 6 | 8.99 |
| Example 7 | 9.14 |
| Example 8 | 9.23 |
| Example 11 | 8.92 |
| Example 12 | 8.77 |
| Example 13 | 8.96 |

TABLE 2

| In vivo agonist and antagonist activity to $5HT_{1A}$ receptors | | | | | | |
|---|---|---|---|---|---|---|
| STFs | FBP | | CS secretion | HYPO- THERMIA | DD 8-OH-DPAT | |
| $ID_{50}$ | $ED_{50}$ | $ID_{50}$ | $ID_{50}$ | $ID_{50}$ | $ED_{50}$ | $ID_{50}$ |

|  | MED alone | (95% CL) + DPAT | (95% CL) alone | (95% CL) + DPAT | MED alone | (95% CL) + DPAT | MED alone | (95% CL) + DPAT | (95% CL) alone | (95% CL) + DPAT |
|---|---|---|---|---|---|---|---|---|---|---|
| Busiprone | >40.0 | 3.7 (1.4–9.8) | 7.4 (2.2–25.6) | >10.0 | 2.5 | >10.0 | 2.5 | >10.0 | 1.35 (0.31–2.5) | >2.5 (0.63–2.5) |
| % MPA |  | 86 |  | 0 |  | 0 |  | 0 |  |  |
| Example 1 | >10.0 | 0.12 (0.03–0.48) | >10.0 | 0.48 (0.19–1.25) | 10.0 | 0.43 (0.2–0.87) | 10.0 | 0.16 (0.05–0.53) | >25 (2.5) | 0.63 (0.16–2.5) |
| % MPA |  | 92 |  | 100 |  | 100 |  | 98 |  | 100 |
| Example 3 |  | <0.16 | <10.0 | 1.60 (0.46–5.58) | >10.0 | 1.56 (0.82–2.98) | >2.5 | 0.50 (0.17–1.46) |  |  |
| % MPA |  |  |  | 100 |  | 100 |  |  |  |  |
| Example 5 |  |  | >2.5 | <2.5 | >2.5 | 2.5 | >10.0 | 0.32 |  |  |
| Example 11 |  |  | >2.5 | <2.5 | >2.5 | 2.5 | >2.5 | 0.16 |  |  |
| Example 12 |  |  | >2.5 | <2.5 | >2.5 | 2.5 | >2.5 | 0.63 |  |  |

STFs = (Spontaneous tail flicks)?
FBP = (Flat body posture)
CS = Corticosterone
DD = Drug discrimination
MED = Minimum effective dose (compared with control)
$ID_{50}$ = Inhibiting dose (50% inhibition)
$ED_{50}$ = Effective dose (50% effect)
95% CL = 95% confidence limit
% MPA = % maximum possible antagonism
The molecules were evaluated alone and against 8-OH-DPAT (0.63 mg/kg s.c.)

C) Conclusion

Examination of the results reported in Tables 1 and 2 show first that the products of the invention have an affinity for the $5HT_{1A}$ receptor that is distinctly greater than that of buspirone and, moreover, that the compounds of the present invention have a $5HT_{1A}$ receptor antagonist behaviour in contrast to buspirone which, although also being bound to the $5HT_{1A}$ receptors, has an agonist behaviour.

It is for that reason that the compounds of the present invention are of value in the treatment of disorders of the central nervous system and neuroendocrinal disorders.

We claim:

1. A 1,4-disubstituted piperazine selected from those of formula I:

R—D—N⏜N—⌬  (I)
        O\\A/B wherein:

R represents:

[structures shown: thiophene; naphthalene; bis-thiophene; benzothiophene; cyclopenta-fused thiophene with $(CH_2)_n$; another bicyclic thiophene structure]

in which n is 3 or 4;

D represents a single bond, except when R represents naphthyl, or a hydrocarbon chain having from 1 to 8 carbon atoms inclusive which is straightchain or branched by a gem-dimethyl; and —A—B— represents:

$-(CH_2)_2-O-$, $-(CH_2)_3-O-$, or $-\underset{\underset{O}{\|}}{C}-CH=CH-$ in racemic or optically active form, and its physiologically tolerable salts with a pharmaceutically-acceptable acid.

2. A compound of claim 1, which is selected from: 4-(benzodioxan-5-yl)-1-[ 4-(thiophen-3-yl)propyl]piperazine, and its physiologically-tolerable acid addition salts.

3. A compound of claim 1, which is selected from: (R,S)-4-(benzodioxan-5-yl)- 1-[(cyclopenta[b]thiophen-5-yl)methyl]piperazine, and its physiologically-tolerable acid addition salts.

4. A compound of claim 1, which is selected from: 4-(benzodioxan-5-yl)-1-[ 2-(naphth-1-yl)ethyl]piperazine, and its physiologically tolerable acid addition salts.

5. A compound of claim 1, which is selected from: 4-(benzodioxan-5-yl)-1-[ 2-(naphth-2-yl)ethyl]piperazine, and its physiologicallytolerable acid addition salts.

6. A compound of claim 1, which is selected from: 4-(benzodioxan-5-yl)-1-[ 2-(benzo[b]thiophen-3-yl)ethyl] piperazine, and its physiologically tolerable acid addition salts.

7. A compound of claim 1, which is : 4-(benzodioxan-5-yl)-1-[ 2-(thieno[2,3-b]thiophen-2-yl)ethyl]piperazine.

8. A compound of claim 1, which is selected from: 4-(benzodioxan-5-yl)-1-[ 2-(thiophen-3-yl)ethyl]piperazine, and its physiologically-tolerable acid addition salts.

9. A pharmaceutical composition useful as a $5-HT_{1A}$ serotinin receptor antagonist, comprising as active ingredient an effective amount of a compound as claimed in claim 1 together with one or more pharmaceutically-acceptable excipient.

10. A method for treating a mammal suffering from anxieity or depression, comprising the step of administering to the said mammal an amount of a 1,4-disubstituted piperazine selected from those of formula I:

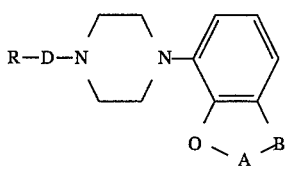

wherein:

R represents:

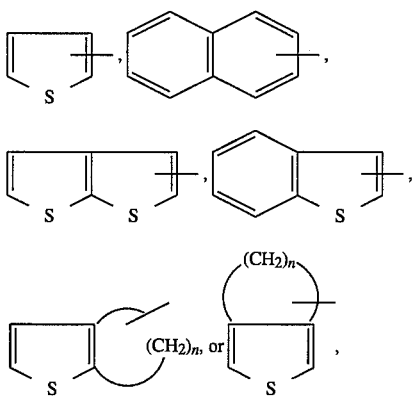

in which n is 3 or 4;

D represents a single bond or a hydrocarbon chain having 1 to 8 carbon atoms inclusive which is straight-chain or branched by a gem-dimethyl; and —A—B— represents:

—(CH$_2$)$_2$—O—, —(CH$_2$)$_3$—O—, or —CO—CH=CH—, in racemic or optically active form, and its physiologically-tolerable salts with a pharmaceutically-acceptable acid, which is effective for alleviation of the said anxiety and depression.

11. A method of claim 10, wherein the compound employed is selected from 4-(benzodioxan-5-yl)-1-[3-(thiophen-3-yl)propyl]-piperazine, and its physiologically-tolerable acid addition salts.

12. A method of claim 10, wherein the compound employed is selected from (R,S)-4-(benzodioxan-5-yl)-1-[(cyclopenta[b]-thiophen- 5-yl)methyl]piperazine, and its physiologicallytolerable acid addition salts.

13. A method of claim 10, wherein the compound employed is selected from 4-(benzodioxan-5-yl)-1-[2-(benzo[b]thiophen-3-yl)ethyl]piperazine, and its physiologically-tolerable acid addition salts.

14. A method of claim 10, wherein the compound employed is 4-(benzodioxan-5-yl)-1-[2-(thieno[2,3-b]thiophen-2-yl)ethyl]piperazine.

15. A method of claim 10, wherein the compound employed is selected from 4-(benzodioxan-5-yl)-1-[2-(thiophen-3-yl)ethyl]piperazine, and its physiologically-tolerable acid addition salts.

* * * * *

UNITED STATES PATENT AND TRADEMARK OFFICE
CERTIFICATE OF CORRECTION

PATENT NO. : 5,464,834
DATED : November 7, 1995
INVENTOR(S) : Jean-Louis Peglion, Bertrand Goument, Mark Millan, Jean-Michel Rivet.

Page 1 of 5

It is certified that error appears in the above-indentified patent and that said Letters Patent is hereby corrected as shown below:

Title Page, [56] OTHER PUBLICATIONS, line 3:
"Alzeheimer's" should read -- Alzheimer's --.

Title Page, Column 2, line 16 from top: "Heuschen" should read -- Hueschen --. Name of firm: Gordon W. Hueschen.

Column 1, line 30, Part of formula is missing.
Insert

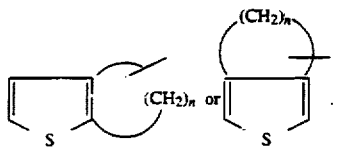

Column 2, line 12: "HT1A" should read -- $5HT_{1A}$ --.

Column 3, line 7: "v" should read -- V --.

Column 3, line 36: "wiley" should read -- Wiley --.

Column 4, line 20: "wiley" should read -- Wiley --

UNITED STATES PATENT AND TRADEMARK OFFICE
CERTIFICATE OF CORRECTION

PATENT NO. : 5,464,834
DATED : November 7, 1995
INVENTOR(S) : Jean-Louis Peglion, Bertrand Goument, Mark Millan, Jean-Michel Rivet.

It is certified that error appears in the above-indentified patent and that said Letters Patent is hereby corrected as shown below:

Column 5, line 30: "6,664" should read -- 6.664"

Column 6, line 61 "((yield:" should read -- (yield: --.

Column 8, line 32: ".." should read -- , --.

Column 8, line 39: "thio are obtained phen" should read -- thiophen --.

Column 8, line 40: "dihydrochloride" should read --dihydrochloride are obtained --.

Column 8, line 48: Delete "[" from end of line.

Column 8, line 49: Add "[" to beginning of line.

Column 9, line 25: "4-benzodioxan-    5-yl)" should read -- 4-benzodioxan-5-yl) --.

Column 11, line 4: Add "." (a period) to end of line.

Column 13, line 66: "-2yl)" should read -- -2-yl).

UNITED STATES PATENT AND TRADEMARK OFFICE
CERTIFICATE OF CORRECTION

PATENT NO. : 5,464,834
DATED : November 7, 1995
INVENTOR(S) : Jean-Louis Peglion, Bertrand Goument, Mark Millan, Jean-Michel Rivet.

Page 3 of 5

It is certified that error appears in the above-indentified patent and that said Letters Patent is hereby corrected as shown below:

Column 16, line 32: "-1[" should read -- -1-[ --.

Column 17, line 23: "-1(" should read -- -1-( --.

Column 17, line 58: "$HT_{1A}$" should read -- $5HT_{1A}$ --.

Column 18, line 58: "12.300" should read -- 12.30, --.

Column 22, line 5 from top: "(0.63-2.5)" should be deleted.

Column 22, line 6 from top: Add -- (0.63-2.5) -- to last column.

Column 22, line 24: Delete "from". (Claim 1, line 10).

Column 22, line 38: "-1-[  4-" should read -- -1-[3- --.

Column 22, line 46: Add a " - " (a dash) after "physiologically".

UNITED STATES PATENT AND TRADEMARK OFFICE
CERTIFICATE OF CORRECTION

PATENT NO. : 5,464,834
DATED : November 7, 1995
INVENTOR(S) : Jean-Louis Peglion, Bertrand Goument, Mark Millan, Jean-Michel Rivet.

It is certified that error appears in the above-indentified patent and that said Letters Patent is hereby corrected as shown below:

Column 22, line 49: Add a "-"(a dash) after "physiologically".

Column 22, line 52: Add a "-" (a dash) after "physiologically".

Column 22, line 62: Delete "one or more".

Column 22, line 62: "together with" should read -- together with a --.

Column 24, line 12: Delete "[" from end of line.

Column 24, line 13: Add "[" to beginning of the line.

UNITED STATES PATENT AND TRADEMARK OFFICE
CERTIFICATE OF CORRECTION

PATENT NO. : 5,464,834
DATED : November 7, 1995
INVENTOR(S) : Jean-Louis Peglion, Bertrand Goument, Mark Millan, Jean-Michel Rivet.

It is certified that error appears in the above-indentified patent and that said Letters Patent is hereby corrected as shown below:

Column 24, line 18: Add a "-" (a dash) after "physiologically".

Column 24, line 20: Delete "[" from end of line.

Column 24, line 21: Add "[" to the beginning of the line.

Signed and Sealed this

Thirteenth Day of February, 1996

Attest:

BRUCE LEHMAN

Attesting Officer      Commissioner of Patents and Trademarks